United States Patent
Lacovara et al.

(10) Patent No.: US 12,377,229 B2
(45) Date of Patent: *Aug. 5, 2025

(54) NON-NICOTINE ELECTRONIC VAPING DEVICE

(71) Applicant: Altria Client Services LLC, Richmond, VA (US)

(72) Inventors: Robert C. Lacovara, Richmond, VA (US); Phillip Diana, Richmond, VA (US); Nam Tran, North Chesterfield, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/461,881

(22) Filed: Sep. 6, 2023

(65) Prior Publication Data

US 2023/0405242 A1 Dec. 21, 2023

Related U.S. Application Data

(63) Continuation of application No. 16/929,507, filed on Jul. 15, 2020, now Pat. No. 11,771,849.

(51) Int. Cl.
*A24F 47/00* (2020.01)
*A24F 40/10* (2020.01)
(Continued)

(52) U.S. Cl.
CPC .......... *A61M 11/041* (2013.01); *A24F 40/10* (2020.01); *A24F 40/51* (2020.01); *A24F 40/53* (2020.01);
(Continued)

(58) Field of Classification Search
CPC .......... A24F 40/50; A24F 40/51; A24F 40/53
See application file for complete search history.

(56) References Cited

U.S. PATENT DOCUMENTS

| 8,757,147 B2 | 6/2014 | Terry et al. |
| 9,072,321 B2 | 7/2015 | Liu |

(Continued)

FOREIGN PATENT DOCUMENTS

| EP | 2468117 A1 | 6/2012 |
| EP | 3620069 A1 | 3/2020 |

(Continued)

OTHER PUBLICATIONS

U.S. Notice of Allowance for U.S. Appl. No. 18/159,374, dated Oct. 9, 2024.

(Continued)

*Primary Examiner* — Eric Yaary
(74) *Attorney, Agent, or Firm* — Harness, Dickey & Pierce, P.L.C.

(57) ABSTRACT

In the non-nicotine electronic vaping device, a saturation sensor measures at least one electrical characteristic of the wick between the heating element and the probe wire at a first time and a second time, wherein the at least one electrical characteristic includes a resistance, a capacitance, or both a resistance and a capacitance. Control circuitry is configured to cause the non-nicotine e-vaping device to: calculate a refill rate at which the non-nicotine pre-vapor formulation flows onto the wick based on the at least one electrical characteristic at the first time and the at least one electrical characteristic at the second time; determine that the refill rate is less than a threshold refill rate; and output a low non-nicotine pre-vapor formulation alert in response to determining that the refill rate is less than the threshold refill rate.

22 Claims, 11 Drawing Sheets

(51) Int. Cl.
  *A24F 40/51* (2020.01)
  *A24F 40/53* (2020.01)
  *A61M 11/04* (2006.01)
  *A61M 15/06* (2006.01)
  *A61M 15/00* (2006.01)

(52) U.S. Cl.
  CPC ......... *A61M 15/06* (2013.01); *A61M 15/0025* (2014.02); *A61M 2205/18* (2013.01); *A61M 2205/3327* (2013.01); *A61M 2205/36* (2013.01); *A61M 2205/52* (2013.01); *A61M 2205/587* (2013.01); *A61M 2205/8206* (2013.01)

(56) References Cited

U.S. PATENT DOCUMENTS

| | | | |
|---|---|---|---|
| 9,289,014 | B2 | 3/2016 | Tucker et al. |
| 9,993,025 | B2 | 6/2018 | Alarcon et al. |
| 10,721,967 | B2 | 7/2020 | Raichman |
| 2013/0192623 | A1 | 8/2013 | Tucker et al. |
| 2015/0305410 | A1 | 10/2015 | Liu |
| 2016/0157523 | A1 | 6/2016 | Liu |
| 2016/0309785 | A1 | 10/2016 | Holtz |
| 2016/0309786 | A1 | 10/2016 | Holtz et al. |
| 2017/0006917 | A1 | 1/2017 | Alvarez |
| 2017/0035110 | A1 | 2/2017 | Keen |
| 2017/0231278 | A1 | 8/2017 | Mironov et al. |
| 2017/0258137 | A1 | 9/2017 | Smith et al. |
| 2017/0325502 | A1 | 11/2017 | Nelson et al. |
| 2019/0269176 | A1 | 9/2019 | Dahlmann |

FOREIGN PATENT DOCUMENTS

| | | |
|---|---|---|
| JP | 2016525367 A | 8/2016 |
| JP | 2017532011 A | 11/2017 |
| JP | 2018529319 A | 10/2018 |
| JP | 2020505002 A | 2/2020 |
| RU | 2704891 C2 | 10/2019 |
| RU | 2704940 C2 | 10/2019 |
| RU | 2707794 C2 | 11/2019 |
| RU | 2719243 C2 | 4/2020 |
| WO | WO-2016/119145 A1 | 8/2016 |
| WO | 2022013398 A2 | 1/2022 |

OTHER PUBLICATIONS

International Search Report and Written Opinion for corresponding Application No. PCT/US2021/037334, dated Sep. 24, 2021.
International Preliminary Report on Patentability and Written Opinion for corresponding Application No. PCT/US2021/037334, dated Jan. 26, 2023.
International Search Report and Written Opinion for corresponding Application No. PCT/EP2021/069857, dated Jan. 12, 2022.
U.S. Restriction Requirement for U.S. Appl. No. 16/929,590, dated Aug. 3, 2022.
U.S. Notice of Allowance for U.S. Appl. No. 16/929,590, dated Oct. 27, 2022.
U.S. Office Action for U.S. Appl. No. 18/159,374, dated Jul. 18, 2024.
Russian Office Action for Application No. 2023103221, dated Nov. 20, 2024, with English translation.
Japanese Office Action for Application No. 2023-502661, dated May 27, 2025, with English translation.

NON-NICOTINE ELECTRONIC VAPING DEVICE

CROSS-REFERENCE TO RELATED APPLICATION

The present application is a continuation under 35 U.S.C. § 120 of U.S. application Ser. No. 16/929,507, filed on Jul. 15, 2020, the entire contents of each of which are hereby incorporated herein by reference.

BACKGROUND

Field

The present disclosure relates to a non-nicotine electronic vaping or e-vaping device.

Description of Related Art

A non-nicotine electronic vaping or e-vaping device includes a heating element that vaporizes a non-nicotine pre-vapor formulation to produce a non-nicotine vapor.

A non-nicotine e-vaping device includes a power supply, such as a rechargeable battery, arranged in the device. The power supply is electrically connected to the heater. The power supply provides power to the heater such that the heater heats to a temperature sufficient to convert the non-nicotine pre-vapor formulation to a non-nicotine vapor. The non-nicotine vapor exits the non-nicotine e-vaping device through a mouthpiece including at least one outlet.

SUMMARY

At least one example embodiment provides a non-nicotine e-vaping device comprising: a non-nicotine reservoir configured to hold non-nicotine pre-vapor formulation; a wick configured to draw non-nicotine pre-vapor formulation from the non-nicotine reservoir; a heating element configured to heat the non-nicotine pre-vapor formulation drawn from the non-nicotine reservoir; a probe wire along a length of the wick, the probe wire being separated from the heating element by the wick; a saturation sensor; and control circuitry. The saturation sensor is configured to: measure at least one electrical characteristic of the wick between the heating element and the probe wire at a first time, the at least one electrical characteristic including a resistance, a capacitance, or both a resistance and a capacitance; and measure the at least one electrical characteristic of the wick between the heating element and the probe wire at a second time, the second time being subsequent to the first time. The control circuitry is configured to cause the non-nicotine e-vaping device to: calculate a refill rate at which the non-nicotine pre-vapor formulation flows onto the wick based on the at least one electrical characteristic at the first time and the at least one electrical characteristic at the second time; determine that the refill rate is less than a threshold refill rate; and output a low non-nicotine pre-vapor formulation alert in response to determining that the refill rate is less than the threshold refill rate.

According to at least some example embodiments, the control circuitry may be configured to cause the non-nicotine e-vaping device to calculate the refill rate based on a difference between the at least one electrical characteristic at the first time and the at least one electrical characteristic at the second time.

The control circuitry may be configured to cause the non-nicotine e-vaping device to: compute a first impedance based on the at least one electrical characteristic at the first time; compute a second impedance based on the at least one electrical characteristic at the second time; and calculate the refill rate based on a difference between the first impedance and the second impedance.

The control circuitry may be configured to cause the non-nicotine e-vaping device to: measure the at least one electrical characteristic of the wick between the heating element and the probe wire at a third time; determine that the at least one electrical characteristic at the third time is greater than or equal to a threshold value; and disable vaping at the non-nicotine e-vaping device in response to determining that the at least one electrical characteristic at the third time is greater than or equal to the threshold value.

The control circuitry may be configured to cause the non-nicotine e-vaping device to: measure the at least one electrical characteristic of the wick between the heating element and the probe wire at a third time; determine that the at least one electrical characteristic at the third time is greater than or equal to a threshold value; and output a low non-nicotine pre-vapor formulation alert in response to determining that the at least one electrical characteristic at the third time is greater than or equal to the threshold value.

The control circuitry may be configured to cause the non-nicotine e-vaping device to: measure the at least one electrical characteristic of the wick between the heating element and the probe wire at a third time; compute an impedance of the wick based on the at least one electrical characteristic at the third time; determine that the impedance is greater than or equal to a threshold value; and disable vaping at the non-nicotine e-vaping device in response to determining that the impedance is greater than or equal to the threshold value.

The control circuitry may be configured to cause the non-nicotine e-vaping device to: measure the at least one electrical characteristic of the wick between the heating element and the probe wire at a third time; compute an impedance of the wick based on the at least one electrical characteristic at the third time; determine that the impedance is greater than or equal to a threshold value; and output a low non-nicotine pre-vapor formulation alert in response to determining that the impedance is greater than or equal to the threshold value.

The non-nicotine e-vaping device may further include a power supply configured to provide power to the non-nicotine e-vaping device.

The probe wire may be a stainless steel wire.

At least one other example embodiment provides a non-nicotine e-vaping device comprising: an outer housing; an inner tube coaxially positioned within the outer housing; a non-nicotine reservoir configured to hold a non-nicotine pre-vapor formulation, the non-nicotine reservoir positioned between the inner tube and the outer housing; a wick configured to draw non-nicotine pre-vapor formulation from the non-nicotine reservoir; a heating element configured to heat the non-nicotine pre-vapor formulation drawn from the non-nicotine reservoir; a saturation sensor assembly; and control circuitry. The saturation sensor assembly is configured to measure at least one electrical characteristic between the outer housing and the inner tube at a first time and a second time, the second time being subsequent to the first time. The control circuitry is configured to cause the non-nicotine e-vaping device to: calculate a refill rate at which the non-nicotine pre-vapor formulation flows onto the wick based on the at least one electrical characteristic at the first time and the at least one electrical characteristic at the second time; determine that the refill rate is less than a threshold refill rate; and output a low non-nicotine pre-vapor formulation alert in response to determining that the refill rate is less than the threshold refill rate.

The non-nicotine e-vaping device may further include a probe wire around the outer perimeter of the inner tube, wherein the saturation sensor assembly may be configured to measure the at least one electrical characteristic between the outer housing and the inner tube by measuring the at least one electrical characteristic between the outer housing and the probe wire around the outer perimeter of the inner tube. The probe wire may be a stainless steel wire.

The control circuitry may be configured to cause the non-nicotine e-vaping device to calculate the refill rate based on a difference between the at least one electrical characteristic at the first time and the at least one electrical characteristic at the second time.

The control circuitry may be configured to cause the non-nicotine e-vaping device to: compute a first impedance based on the electrical characteristic at the first time; compute a second impedance based on the electrical characteristic at the second time; and calculate the refill rate based on a difference between the first impedance and the second impedance.

The control circuitry may be configured to cause the non-nicotine e-vaping device to: measure the at least one electrical characteristic of the wick between the heating element and the inner tube at a third time; determine that the at least one electrical characteristic at the third time is greater than or equal to a threshold value; and disable vaping at the non-nicotine e-vaping device in response to determining that the at least one electrical characteristic at the third time is greater than or equal to the threshold value.

The control circuitry may be configured to cause the non-nicotine e-vaping device to: measure the at least one electrical characteristic of the wick between the heating element and the inner tube at a third time; determine that the at least one electrical characteristic at the third time is greater than or equal to a threshold value; and output a low non-nicotine pre-vapor formulation alert in response to determining that the at least one electrical characteristic at the third time is greater than or equal to the threshold value.

The control circuitry is configured to cause the non-nicotine e-vaping device to: measure the at least one electrical characteristic of the wick between the heating element and the inner tube at a third time; compute an impedance of the wick based on the at least one electrical characteristic at the third time; determine that the impedance is greater than or equal to a threshold value; and disable vaping at the non-nicotine e-vaping device in response to determining that the impedance is greater than or equal to the threshold value.

The control circuitry may be configured to cause the non-nicotine e-vaping device to: measure the at least one electrical characteristic of the wick between the heating element and the inner tube at a third time; compute an impedance of the wick based on the at least one electrical characteristic at the third time; determine that the impedance is greater than or equal to a threshold value; and output a low non-nicotine pre-vapor formulation alert in response to determining that the impedance is greater than or equal to the threshold value.

At least one other example embodiment provides a method for detecting depletion of non-nicotine pre-vapor formulation in a non-nicotine reservoir of a non-nicotine e-vaping device, the method comprising: measuring at least one electrical characteristic of a wick between a heating element and a probe wire at a first time, the at least one electrical characteristic including a resistance, a capacitance, or both a resistance and a capacitance; measuring the at least one electrical characteristic of the wick between the heating element and the probe wire at a second time, the second time being subsequent to the first time; calculating a refill rate at which non-nicotine pre-vapor formulation flows onto the wick based on the at least one electrical characteristic at the first time and the at least one electrical characteristic at the second time; determining that the refill rate is less than a threshold refill rate; and outputting a low non-nicotine pre-vapor formulation alert in response to determining that the refill rate is less than the threshold refill rate.

According to at least some example embodiments the method may further include: measuring the at least one electrical characteristic of the wick between the heating element and the probe wire at a third time; determining that the at least one electrical characteristic at the third time is greater than or equal to a threshold value; and disabling vaping at the non-nicotine e-vaping device in response to determining that the at least one electrical characteristic at the third time is greater than or equal to the threshold value.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
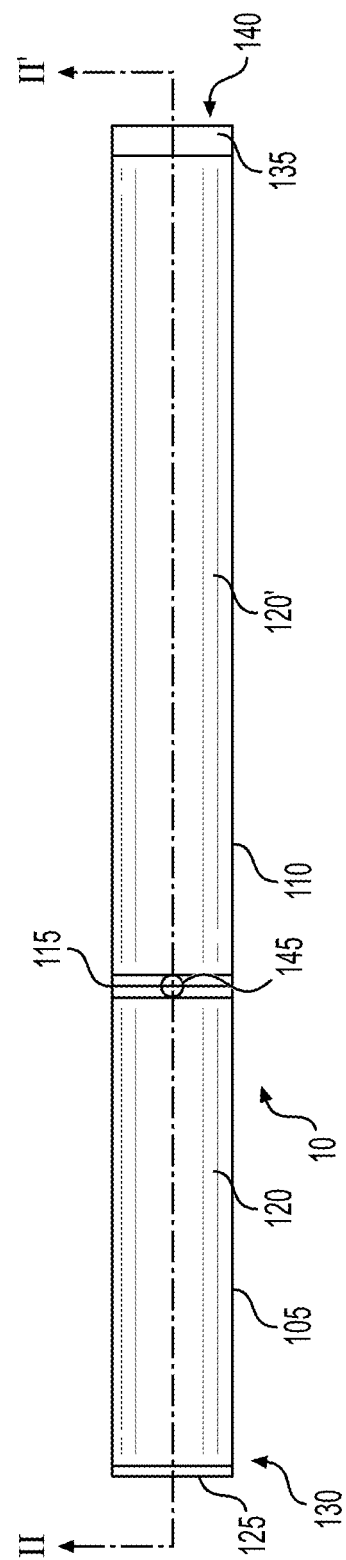
FIG. 1 is a side view of a non-nicotine electronic vaping or e-vaping device according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments Like numbers refer to like elements throughout the description of the figures.

FIG. 1 is a side view of a non-nicotine e-vaping device according to at least one example embodiment.

Referring to FIG. 1, in at least one example embodiment, a non-nicotine electronic vaping device (e-vaping device) 10 includes a replaceable cartridge (or first section) 105 and a reusable battery section (or second section) 110. The first section 105 and the second section 110 may be coupled together at a connector assembly 115.

In at least one example embodiment, the connector assembly 115 may be a connector as described in U.S. application Ser. No. 15/154,439, filed May 13, 2016, the entire contents of which are incorporated herein by reference thereto. As described in U.S. application Ser. No. 15/154,439, the connector assembly 115 may be formed by a deep drawn process.

In the example embodiment shown in FIG. 1, the first section 105 includes a first housing 120 and the second section 110 includes a second housing 120'. The non-nicotine e-vaping device 10 includes a mouthpiece 125 at a first end 130, and an end cap 135 at a second end 140.

According to at least one example embodiment, the first housing 120 and the second housing 120' may have a generally cylindrical cross-section. In other example embodiments, the housings 120 and 120' may have a generally triangular, rectangular, oval, square, or polygonal cross-section along one or more of the first section 105 and the second section 110. Furthermore, the housings 120 and 120' may have the same or different cross-section shape, or the same or different size. As discussed herein, the housings 120, 120' may also be referred to as outer or main housings.

Although example embodiments may be described in some instances with regard to the first section 105 coupled to the second section 110, example embodiments should not be limited to these examples.

Figure 2:
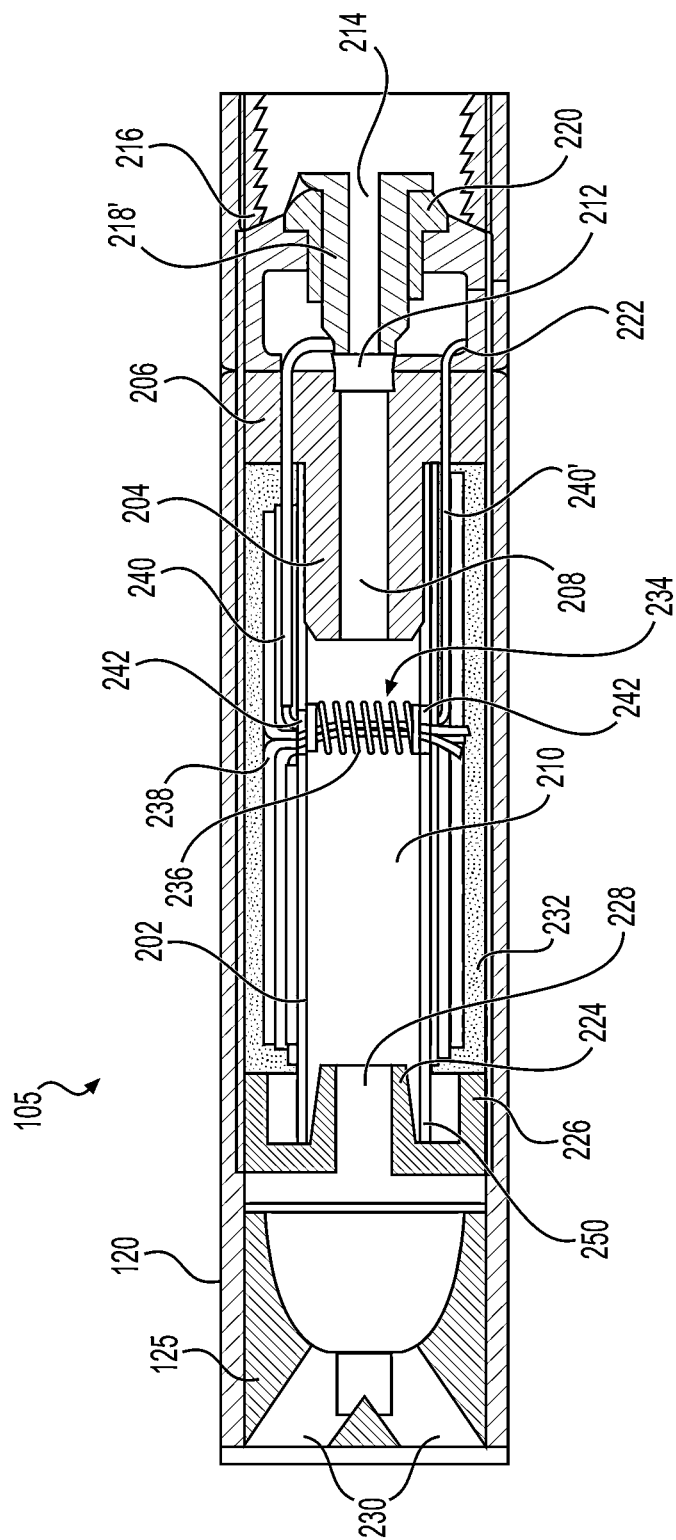
FIG. 2 is a cross-sectional view of an example embodiment of the first section of the non-nicotine e-vaping device shown in FIG. 1 along line II-IT.
Figure 3:
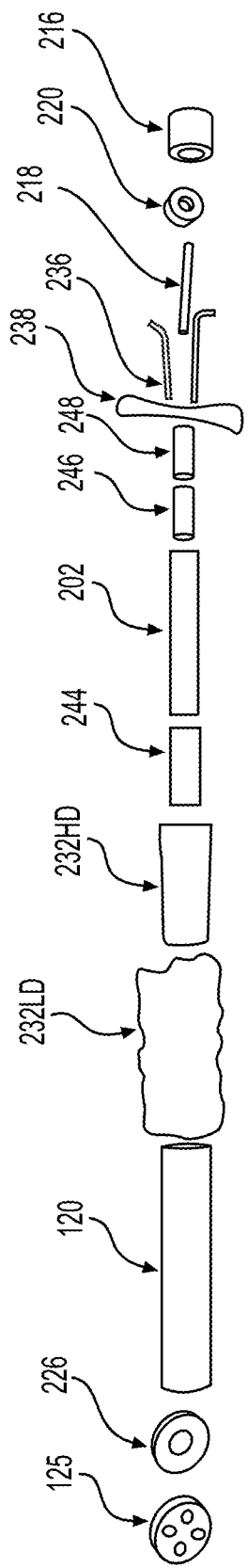
FIG. 3 is an exploded view of an example embodiment of the first section shown in FIG. 2.

FIG. 2 is a cross-sectional view of the first section 105 of the non-nicotine e-vaping device 10 along line II-II in FIG. 1. FIG. 3 is an exploded view of an example embodiment of the first section 105 shown in FIG. 2.

Referring to FIGS. 2 and 3, the first housing 120 extends in a longitudinal direction and an air tube 202 (or chimney) is coaxially positioned within the first housing 120.

A first end portion (e.g., upstream with respect to air flow during vaping) of the air tube 202, a first nose portion 204 of a first gasket 206 (or seal) is fitted into the air tube 202. An outer perimeter of the first gasket 206 may provide a seal with an interior surface of the first housing 120. The first gasket 206 includes a central, longitudinal air passage 208 in fluid communication with the air tube 202 to define an inner passage (also referred to as a central channel or central inner passage) 210. A transverse channel 212 at a backside portion of the first gasket 206 intersects and communicates with the air passage 208 of the first gasket 206. The transverse channel 212 enables fluid communication between the air passage 208 and a central air passage 214, which is discussed in more detail later.

A first connector piece 216 is fitted into a first end of the first housing 120. The first connector piece 216 is part of the connector assembly 115.

The first connector piece 216 is a hollow cylinder with female threads on a portion of the outer lateral surface. The first connector piece 216 is conductive, and may be formed of, or coated with, a conductive material. The female threads (or female threaded section) may be mated with male threads (or a male threaded section) of the second section 110 to connect the first section 105 and the second section 110. However, example embodiments are not limited to this example embodiment. Rather, the connectors may be, for example, snug-fit connectors, detent connectors, clamp connectors, clasp connectors, or the like. Moreover, the positioning of the male and female connectors may be reversed as desired such that the male connector is part of the first section 105.

A conductive post 218 nests within the hollow portion of the first connector piece 216, and is electrically insulated from the first connector piece 216 by a gasket insulator 220. The conductive post 218 may be formed of a conductive material (e.g., stainless steel, copper, or the like) and may serve as an anode portion of the first connector piece 216.

The conductive post 218 defines the central air passage 214. The central air passage 214 is in fluid communication with the air passage 208 via the transverse channel 212. The gasket insulator 220 holds the conductive post 218 within the first connector piece 216. The gasket insulator 220 also electrically insulates the conductive post 218 from an outer portion 222 of the first connector piece 216.

The outer portion 222 of the first connector piece 216 serves as the cathode connector of the first connector piece 216, and the outer portion 222 is electrically insulated from the conductive post 218 by the gasket insulator 220. The outer portion 222 may sometimes be referred to herein as a cathode connector or cathode portion. The outer portion 222 may be formed of a conductive material (e.g., stainless steel, copper, or the like).

Still referring to the example embodiment shown in FIGS. 2 and 3, a second nose portion 224 of a second gasket 226 may be fitted into a second end portion 250 of the air tube 202. An outer perimeter of the second gasket 226 may also provide a substantially tight seal with an interior surface of the first housing 120. The second gasket 226 may include a central passage 228 (or channel) disposed between the inner passage 210 of the air tube 202 and the interior of the mouthpiece 125. Non-nicotine vapor may flow from the inner passage 210 into a cavity within the mouthpiece 125 through the central passage 228.

The mouthpiece 125 includes at least two outlets 230, which may be located off-axis from the longitudinal axis of the non-nicotine e-vaping device 10. The outlets 230 may be recessed or non-recessed and angled outwardly in relation to the longitudinal axis of the non-nicotine e-vaping device 10. The outlets 230 may be substantially uniformly distributed about the perimeter of the mouthpiece 125 so as to substantially uniformly distribute non-nicotine vapor.

The first section 105 further includes a non-nicotine reservoir 232 configured to store a non-nicotine pre-vapor formulation and a vaporizer 234. The vaporizer 234 includes a heating element 236 and a wick 238. The vaporizer 234 is configured to vaporize non-nicotine pre-vapor formulation drawn from the non-nicotine reservoir 232. In the example embodiment shown in FIGS. 2 and 3, the confines of the non-nicotine reservoir 232 are defined between the first gasket 206, the second gasket 226, the first housing 120, and the air tube 202. However, example embodiments should not be limited by this example. The non-nicotine reservoir 232 may contain a non-nicotine pre-vapor formulation, and optionally a storage medium 232LD, 232HD configured to store the non-nicotine pre-vapor formulation therein.

In at least one example embodiment, the storage medium may be a fibrous material including at least one of cotton (e.g., a winding of cotton gauze), polyethylene, polyester, rayon, combinations thereof, or the like. As shown in FIGS. 2 and 3, the storage medium 232LD, 232HD may include two layers of fibrous material. Each layer may have a different density. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In the example embodiment shown in FIG. 3, the storage medium includes a low density gauze 232LD surrounding a high density gauze 232HD. The high density gauze 232HD may be positioned between the low density gauze 232LD and the air tube 202 so that the non-nicotine pre-vapor formulation is drawn toward the wick 238.

In at least one other example embodiment, the non-nicotine reservoir 232 may include a filled tank lacking any storage medium and containing only non-nicotine pre-vapor formulation.

In at least one example embodiment, the non-nicotine reservoir 232 may at least partially surround the inner passage 210 and the air tube 202. The heating element 236 may extend transversely across the inner passage 210 between opposing portions of the non-nicotine reservoir 232. In at least some example embodiments, the heating element 236 may extend parallel to a longitudinal axis of the inner passage 210.

The non-nicotine reservoir 232 may be sized and configured to hold enough non-nicotine pre-vapor formulation such that the non-nicotine e-vaping device 10 may be configured for vaping for at least about 200 seconds. Moreover, the non-nicotine e-vaping device 10 may be configured to allow each puff to last a maximum of about 5 seconds.

As mentioned above, the vaporizer 234 incudes the heating element 236 and the wick 238. The wick 238 may include at least a first end portion and a second end portion, which may extend into opposite sides of the non-nicotine reservoir 232. The heating element 236 may at least partially surround a central portion of the wick 238.

The wick 238 may draw the non-nicotine pre-vapor formulation from the non-nicotine reservoir 232 (e.g., via capillary action), and the heating element 236 may heat the non-nicotine pre-vapor formulation in the central portion of the wick 238 to a temperature sufficient to vaporize the non-nicotine pre-vapor formulation thereby generating a "vapor." As referred to herein, a "vapor" is any matter generated or outputted from any non-nicotine e-vaping device according to any of the example embodiments disclosed herein.

In addition to the features discussed herein, in at least one example embodiment of the non-nicotine e-vaping device 10 may include the features set forth in U.S. Patent Application Publication No. 2013/0192623 to Tucker et al. filed Jan. 31, 2013 and/or features set forth in U.S. patent application Ser. No. 15/135,930 to Holtz et al. filed Apr. 22, 2016, the entire contents of each of which are incorporated herein by reference thereto. In at least one other example embodiment, the non-nicotine e-vaping device may include the features set forth in U.S. patent application Ser. No. 15/135,923 filed Apr. 22, 2016, and/or U.S. Pat. No. 9,289,014 issued Mar. 22, 2016, the entire contents of each of which are incorporated herein by this reference thereto.

In at least one example embodiment, as discussed in more detail later, the non-nicotine pre-vapor formulation is a material or combination of materials that may be transformed into a non-nicotine vapor that is devoid of nicotine.

In at least one example embodiment, the wick 238 may include filaments (or threads) having a capacity to draw the non-nicotine pre-vapor formulation. For example, the wick 238 may be a bundle of glass (or ceramic) filaments, a bundle including a group of windings of glass filaments, or the like, all of which arrangements may be capable of drawing non-nicotine pre-vapor formulation via capillary action by interstitial spacing between the filaments. The filaments may be generally aligned in a direction perpendicular (transverse) to the longitudinal direction of the non-nicotine e-vaping device 10. In at least one example embodiment, the wick 238 may include one to eight filament strands, each strand comprising a plurality of glass filaments twisted together. The end portions of the wick 238 may be flexible and foldable into the confines of the non-nicotine reservoir 232. The filaments may have a cross-section that is generally cross-shaped, clover-shaped, Y-shaped, or in any other suitable shape.

In at least one example embodiment, the wick 238 may include any suitable material or combination of materials. Examples of suitable materials may be, but not limited to, glass, ceramic- or graphite-based materials. The wick 238 may have any suitable capillarity drawing action to accommodate non-nicotine pre-vapor formulations having different physical properties such as density, viscosity, surface tension and vapor pressure. The wick 238 may be non-conductive.

In at least one example embodiment, the heating element 236 may include a coil of wire (a heater coil) which at least partially surrounds the wick 238. The wire used to form the coil of wire may be metal. The heating element 236 may extend fully or partially along the length of the wick 238. The heating element 236 may further extend fully or partially around the circumference of the wick 238. In some example embodiments, the heating element 236 may or may not be in contact (or direct contact) with the wick 238.

In the example embodiment shown in FIGS. 2 and 3, the heating element 236 is electrically connected to the conductive post 218 via a first electrical lead 240, and to the outer portion 222 via a second electrical lead 240'. Accordingly, the outer portion 222 and the conductive post 218 form respective external electrical connection to the heating element 236.

In at least some other example embodiments, the heating element 236 may be in the form of a planar body, a ceramic body, a single wire, a mesh, a cage of resistive wire or any other suitable form. More generally, the heating element 236 may be any heater that is configured to vaporize the non-nicotine pre-vapor formulation.

In at least one example embodiment, the heating element 236 may be formed of any suitable electrically resistive materials. Examples of suitable electrically resistive materials may include, but not limited to, copper, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 236 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 236 may include at least one material selected from the group consisting of stainless steel, copper, copper alloys, nickel-chromium alloys, super alloys and combinations thereof. In an example embodiment, the heating element 236 may be formed of nickel-chromium alloys or iron-chromium alloys. In another example embodiment, the heating element 236 may be a ceramic heater having an electrically resistive layer on an outside surface thereof.

Still referring to FIGS. 2 and 3, the air tube 202 may include a pair of opposing slots 242, such that the wick 238 and the first and second electrical leads 240 and 240' or ends of the heating element 236 may extend out from the respective opposing slots 242. The provision of the opposing slots 242 in the air tube 202 may facilitate placement of the heating element 236 and the wick 238 into position within the air tube 202 without impacting edges of the opposing slots 242 and the coiled section of the heating element 236. Accordingly, edges of the opposing slots 242 may not be allowed to impact and alter the coil spacing of the heating element 236, which would otherwise create potential sources of hotspots. In at least one example embodiment, the air tube 202 may have a diameter of about 4 mm and each of the opposing slots may have major and minor dimensions of about 2 mm by about 4 mm.

In at least one example embodiment, the heating element 236 may heat non-nicotine pre-vapor formulation in the wick 238 by thermal conduction. Alternatively, heat from the heating element 236 may be conducted to the non-nicotine pre-vapor formulation by means of a heat conductive element or the heating element 236 may transfer heat to the incoming ambient air that is drawn through the non-nicotine e-vaping device 10 during vaping, which in turn heats the non-nicotine pre-vapor formulation by convection.

As shown in FIG. 3, the first section 105 may further include a cover tube 244, a spacer tube 246 and an inner tube 248. Although not shown in FIG. 2, the cover tube 244 may be arranged to surround the portion of the air tube 202 between the heating element 236 and the second nose portion 224. As with the air tube 202, the cover tube 244 may extend in the longitudinal direction and may be coaxially positioned within the first housing 120. The cover tube 244 may cover a portion of each of the opposing slots 242.

The spacer tube 246 may extend in the longitudinal direction and be coaxially positioned within the air tube 202 between the heating element 236 and the conductive post 218. The inner tube 248 may extend in the longitudinal direction and be coaxially positioned within the spacer tube 246. Although the cover tube 244, the spacer tube 246 and the inner tube 248 are shown in FIG. 3, one or more of these tubes (e.g., the inner tube 248) may be omitted.

Figure 4:
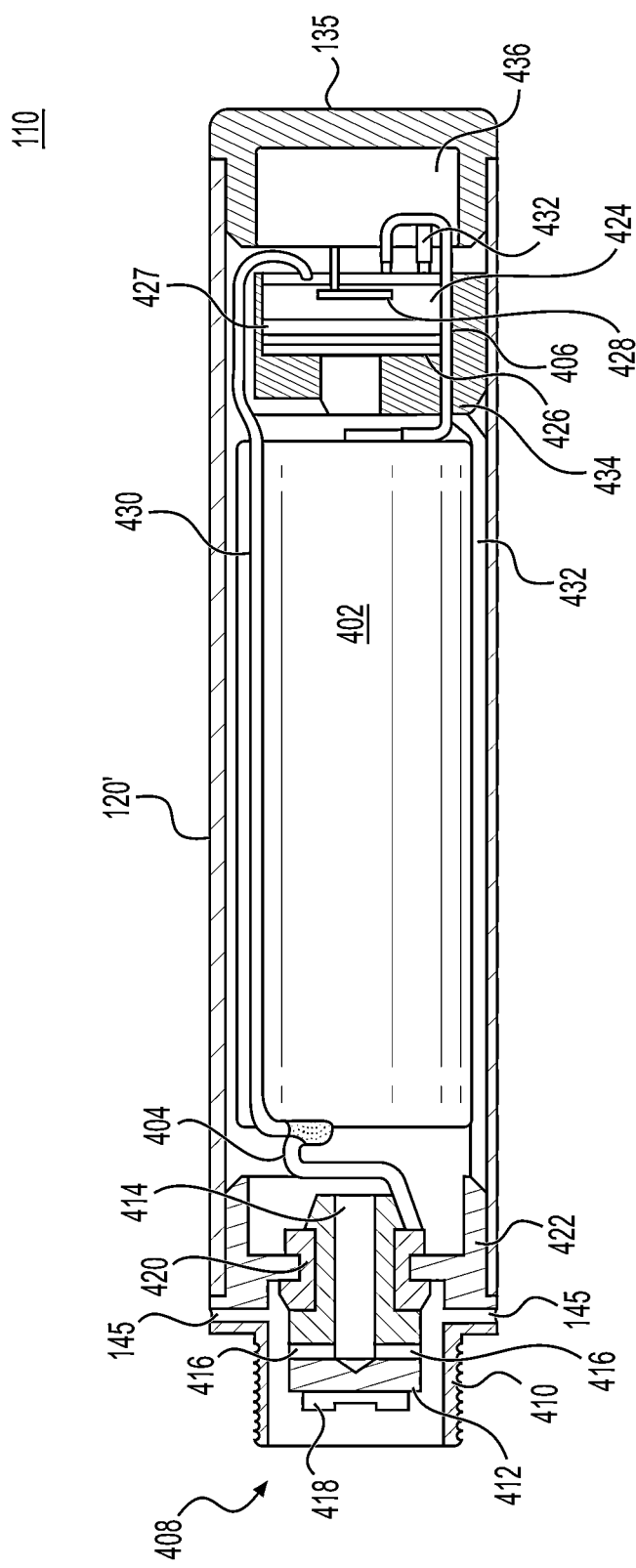
FIG. 4 is a cross-sectional view of an example embodiment of a second section of the electronic vaping device shown in FIG. 1 along line II-IT.
Figure 5:
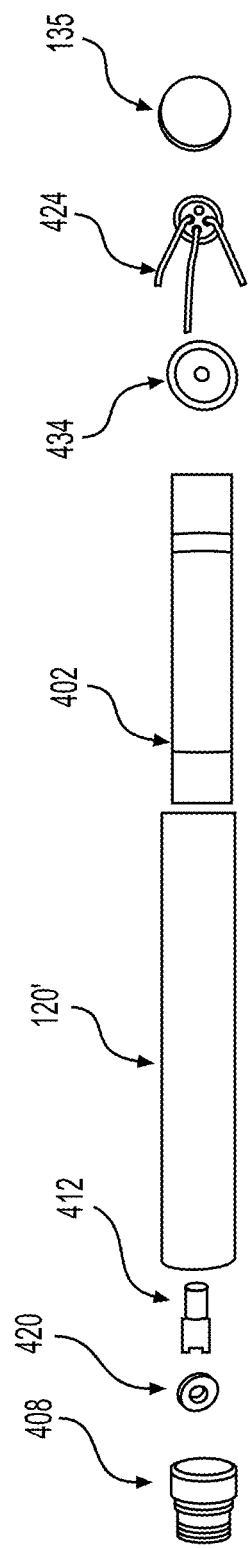
FIG. 5 is an exploded view of an example embodiment of the second section shown in FIG. 4.

FIG. 4 is a cross-sectional view of a second section of an example embodiment of the non-nicotine e-vaping device 10 along line II-IT of FIG. 1. FIG. 5 is an exploded view of an example embodiment of the second section 110 shown in FIG. 4.

The second section 110 may be a reusable section of the non-nicotine e-vaping device 10, wherein the reusable section may be capable of being recharged by an external charging device. Alternatively, the second section 110 may be disposable. In this example, the second section 110 may be used until the energy from a power supply 402 (described below) is depleted (e.g., the energy fails below a threshold level).

Referring to FIGS. 4 and 5, according to at least this example embodiment, the power supply 402 includes an anode connection 404 and a cathode connection 406. Each of the anode connection 404 and the cathode connection 406 may be in the form of one or more electrical leads or wires. The power supply 402 may be a battery. For example, the power supply 402 may be a Lithium-ion battery, or a variant of a Lithium-ion battery, such as a Lithium-ion polymer battery. The battery may either be disposable or rechargeable.

The second section 110 further includes a connector piece 408 at a first end of the second section 110. In the example embodiment shown in FIG. 4, the connector piece 408 is a male connector configured to connect to the female first connector piece 216 of the first section 105. Alternatively, the connector piece 408 may be a female connector configured to connect to a male connector of the first section 105.

In the example embodiment shown in FIG. 4, the connector piece 408 includes threads 410 configured to mate with corresponding threads on the first connector piece 216 of the first section 105. Although illustrated as a threaded connection, according to at least some other example embodiments, the connector piece 408 may be, for example, snug-fit connectors, detent connectors, clamp connectors, clasp connectors, or the like.

The cathode connection (connector piece 408) of the power supply 402 terminates at, and is electrically connected to, a sensor assembly 424 positioned proximate to a second end of the second section 110. The sensor assembly 424 will be discussed in more detail later.

The anode connection 404 terminates at, and is electrically connected to, a conductive post 412. The conductive post 412 may serve as the anode portion of the connector piece 408. The conductive post 412 defines a central passage 414, which is in fluid communication with one or more side vents 416. The side vents 416 may be holes bored into the conductive post 412. The central passage 414 and the one or more side vents 416 allow for puff detection by the sensor assembly (e.g., a puff sensor assembly) 424 resulting from changes in pressure when air is drawn in through air inlets 145.

Although only two side vents 416 and two air inlets 145 are shown in FIG. 4, example embodiments should not be limited to this example. Rather, the conductive post 412 may include any number of side vents 416, and the connector piece 408 may include any number of air inlets 145. For example, the conductive post 412 may include 4 side vents 416 spaced apart at equal distances around the conductive post 412. Similarly, the connector piece 408 may include 4 air inlets 145 spaced apart at equal distances around the connector piece 408.

The conductive post 412 further includes an upper portion 418 having an indentation allowing air drawn through the air inlets 145 to flow and/or communicate through the end of the second section 110 into the first section 105 when connected to the second section 110.

The conductive post 412 may be formed of a conductive material (e.g., stainless steel, copper, or the like), and nested within the hollow portion of the connector piece 408. When the connector piece 408 of the second section 110 is coupled to the first connector piece 216 of the first section 105, the upper portion 418 (and the conductive post 412) physically and electrically connects to the conductive post 218 to allow flow of electrical current from the power supply 402 to the heating element 236. The electrical connection also allows for electrical signaling between the first section 105 and the second section 110.

Still referring to FIGS. 4 and 5, a gasket insulator 420 holds the conductive post 412 within the connector piece 408. The gasket insulator 420 also electrically insulates the conductive post 412 from an outer portion 422 of the connector piece 408. The outer portion 422 may be formed of a conductive material (e.g., stainless steel, copper, or the like) and may serve as a cathode portion of the connector piece 408.

As mentioned above, the connector piece 408 includes one or more air inlets 145 configured to communicate ambient air into the connector piece 408. The air inlets 145 may also be sometimes referred to as vents or air vents.

The ambient air drawn into the connector piece 408 may combine and/or mix with air flowing out of the one or more side vents 416 and flow into the first section 105, when the first section 105 is coupled to the second section 110. In at least one example embodiment, the air inlets 145 may be bored into the connector piece 408 just below the threads 410 at an angle perpendicular or substantially perpendicular to the longitudinal centerline of the connector piece 408.

The sidewalls of the air inlets 145 may be beveled in order to cause the sidewalls to slope inwards (e.g., to "countersink" the sidewalls at the rim of the air inlets 145). By beveling the sidewalls at the rim of the air inlets 145 (as opposed to using relatively sharp edges at the rim of the air inlets 145), the air inlets 145 may be less likely to become clogged or partially blocked (due to a reduction in the effective cross-sectional area of the air inlets 145 near the rim of the air inlets 145). In at least one example embodiment, the sidewalls of the rim of the air inlets 145 may be beveled (inclined) to be about 38 degrees relative to a longitudinal length (or the longitudinal centerline) of the connector piece 408 and the second housing 120' of the second section 110.

In at least one example embodiment, the air inlets 145 may be sized and configured such that the non-nicotine e-vaping device 10 has a resistance-to-draw (RTD) in the range of from about 60 mm $H_2O$ to about 150 mm $H_2O$.

Referring still to FIGS. 4 and 5, as mentioned above, the second section 110 includes a sensor assembly (e.g., a puff sensor assembly) 424.

As shown in FIG. 4, for example, the sensor assembly 424 is electrically connected and powered by the power supply 402. In at least this example embodiment, the sensor assembly 424 includes a sensor (e.g., a puff sensor) 426, a saturation sensor 427, and control circuitry 428.

The control circuitry 428 is configured to provide an electrical current and/or electrical signaling to the first section 105. To this end, the control circuitry 428 is electrically connected to the conductive post 412 (anode portion of the connector piece 408) via control circuitry wiring (or lead) 430, and to the outer (cathode) portion 422 of the connector piece 408 via control circuitry wiring (or lead) 432. In at least this example embodiment, the control circuitry wiring 432 acts as a cathode for the electrical circuit including the sensor assembly 424.

The sensor 426 may be a capacitive sensor capable of sensing an internal pressure drop within the second section 110. The sensor 426 and the control circuitry 428 may function together to open and close a heater control circuit (not shown) between the power supply 402 and the heating element 236 of the first section 105 when coupled to the second section 110. In at least one example embodiment, the sensor 426 is configured to generate an output indicative of a magnitude and direction of airflow through the non-nicotine e-vaping device 10. In this example, the control circuitry 428 receives the output of the sensor 426, and determines if (1) the direction of the airflow indicates an application of negative pressure to (e.g., draw on) the mouthpiece 125 (versus positive pressure or blowing) and (2) the magnitude of the application of negative pressure exceeds a threshold level. If these vaping conditions are met, then the control circuitry 428 electrically connects the power supply 402 to the heating element 236 to activate the heating element 236.

In one example, the heater control circuit may include a heater power control transistor (not shown). The control circuitry 428 may electrically connect the power supply 402 to the heating element 236 by activating the heater power control transistor. In at least one example, the heater power control transistor (or heater control circuit) may form part of the control circuitry 428.

According to at least one example embodiment, the sensor assembly 424 may include one or more features set forth in U.S. Pat. No. 9,072,321 to Loi Ling Liu and/or U.S. Patent Application Publication No. 2015/0305410 to Loi Ling Liu, the entire contents of each of which are incorporated herein by reference. However, example embodiments should not be limited to this example. Rather, the control circuitry 428 and the sensor 426 may be separate elements arranged on a printed circuit board, and connected via electrical contacts. Additionally, although discussed herein with regard to a capacitive sensor, the sensor 426 may be any suitable pressure sensor, for example, a Microelectromechanical system (MEMS) including a piezo-resistive or other pressure sensor.

As is described in further detail in FIGS. 7-11, the saturation sensor 427 is connected to the power supply 402 via cathode connection 406 and electrical lead 430 and to the first section 105 via electrical lead 432. The saturation sensor 427 may be configured to measure one or more electrical characteristics of a saturation circuit included in the first section 105. According to one or more example embodiments, the saturation sensor 427 may measure a resistance and/or a capacitance of the saturation circuit. From the resistance and/or capacitance, the control circuitry 428 may calculate the impedance of the saturation circuit. In one example, based on the resistance, capacitance and/or impedance, the control circuitry 428 may detect when the non-nicotine pre-vapor formulation in the non-nicotine reservoir 232 is becoming depleted (e.g., the amount of non-nicotine pre-vapor formulation in the non-nicotine reservoir falls below a first minimum threshold level) and generate an alert accordingly. In another example, the control circuitry 428 may cause the non-nicotine e-vaping device 10 to disable vaping and/or power off when depletion of the non-nicotine pre-vapor formulation in the non-nicotine reservoir is detected (e.g., the amount of non-nicotine pre-vapor formulation in the non-nicotine reservoir falls below a second minimum threshold level, which is less than the first minimum threshold level).

The control circuitry 428 may include, among other things, a controller. According to one or more example embodiments, the controller may be implemented using hardware, a combination of hardware and software, or storage media storing software. Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

In another example embodiment, the control circuitry 428 may include a manually operable switch for an adult vaper to supply power to the heating element 236.

In at least one example embodiment, the control circuitry 428 may limit the time period during which electrical current is continuously supplied to the heating element 236. The time period may be set or pre-set depending on the amount of non-nicotine pre-vapor formulation desired to be vaporized. In one example, the time period for continuous application of electrical current to the heating element 236 may be limited such that the heating element 236 heats a portion of the wick 238 for less than about 10 seconds. In another example, the time period for continuous application of electrical current to the heating element 236 may be limited such that the heating element 236 heats a portion of the wick 238 for about 5 seconds.

Still referring to FIGS. 4 and 5, the sensor assembly 424 is cradled within a sensor holder 434 at the second end of the second section 110. In at least one example embodiment, the sensor holder 434 may be part of a silicon or rubber gasket. However, example embodiments should not be limited to this example.

A heat activation light 436 may also be arranged to the second end of the second section 110. In the example embodiment shown in FIG. 4, the heat activation light 436 may be arranged within the end cap 135. The heat activation light 436 may include one or more light-emitting diodes (LEDs). The LEDs may include one or more colors (e.g., white, yellow, red, green, blue, or the like). Moreover, the heat activation light 436 may be visible to an adult vaper during vaping, and configured to glow when the power supply 402 supplies electrical current to the heating element 236. The heat activation light 436 may be utilized for the non-nicotine e-vaping system diagnostics or to indicate that recharging of the power supply 402 is in progress. The heat activation light 436 may also be configured such that the adult vaper may activate or deactivate the heat activation light 436 for privacy. The heat activation light 436 may be part of, or electrically connected to, the sensor assembly 424 as described in U.S. Pat. No. 9,072,321 to Loi Ling Liu and/or U.S. Patent Application Publication No. 2015/0305410 to Loi Ling Liu.

Figure 6:
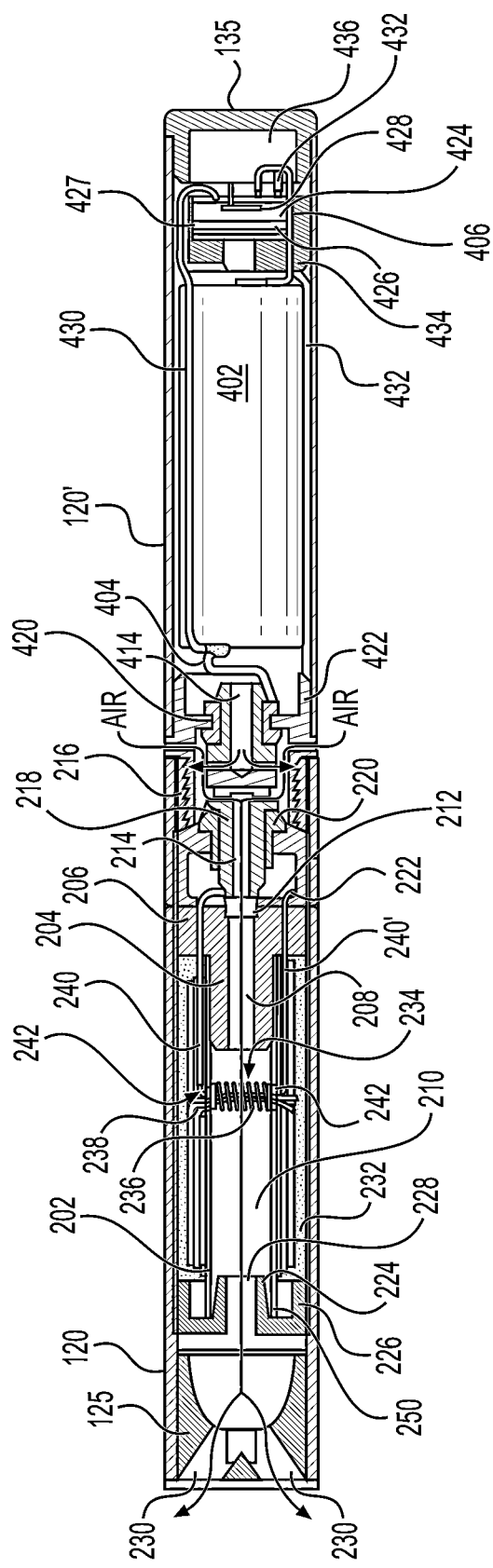
FIG. 6 is a cross-sectional view of an example embodiment of the non-nicotine e-vaping device shown in FIG. 1 along line II-IT.

FIG. 6 is a cross-sectional view of an example embodiment of the non-nicotine e-vaping device shown in FIG. 1 along line II-IT.

In FIG. 6, the first section 105 is shown coupled to the second section 110. The arrows in FIG. 6 indicate example air flow through the non-nicotine e-vaping device 10.

Operation of the non-nicotine e-vaping device 10 to create a non-nicotine vapor when the first section 105 is coupled to the second section 110 will now be described with regard to FIG. 6.

Referring to FIG. 6, air is drawn primarily into the first section 105 through the at least one of the air inlets 145 in response to application of negative pressure to the mouthpiece 125.

If the control circuitry 428 detects the vaping conditions discussed above, then the control circuitry 428 initiates supply of power to the heating element 236, such that the heating element 236 heats non-nicotine pre-vapor formulation on the wick 238 to generate non-nicotine vapor.

The air drawn through the air inlets 145 enters the cavity within the connector piece 408 and passes through the indentation in the upper portion 418 into the central air passage 214. From the central air passage 214, air flows through the transverse channel 212, through the air passage 208, and then through the inner passage 210.

The air flowing through the inner passage 210 combines and/or mixes with the non-nicotine vapor generated by the heating element 236, and the air-non-nicotine vapor mixture passes from the inner passage 210 into the central passage 228 and then into the cavity within the mouthpiece 125. From the cavity in the mouthpiece 125, the air-non-nicotine vapor mixture flows out of the outlets 230.

Figure 7:
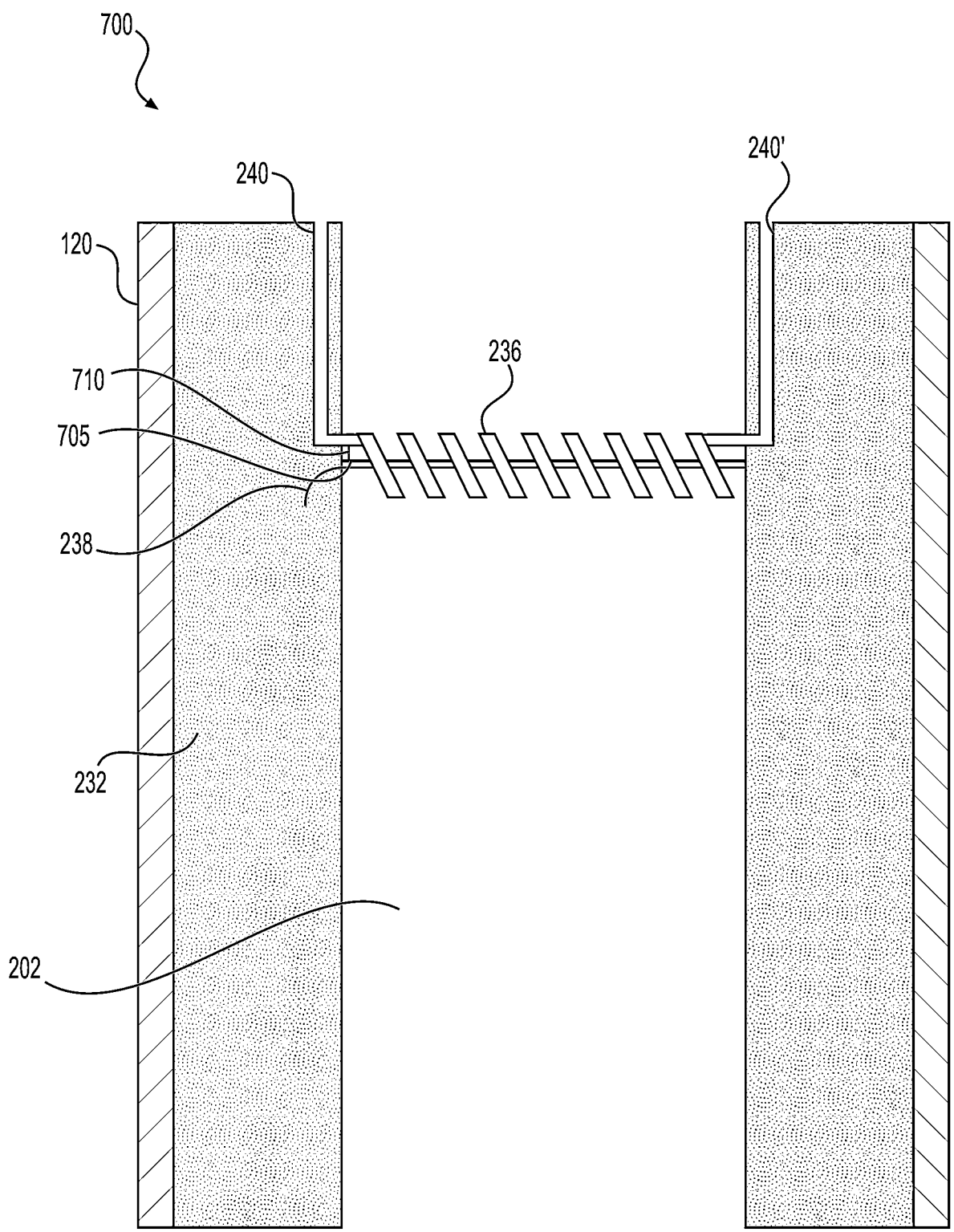
FIG. 7 is a cross-sectional view of an example embodiment of a saturation circuit assembly.

FIG. 7 is a cross-sectional view of an example embodiment of a saturation circuit assembly 700. FIG. 7 depicts a portion of the first section 105 of the non-nicotine e-vaping device 10, enhancing the view of the heating element 236. In at least an example embodiment, the saturation circuit assembly 700 includes a probe wire 705 extending along the length of the wick 238, but separate from (not in contact with) the heating element 236. In various example embodiments, the wick 238 and the probe wire 705 may be shorter or longer than that shown in FIG. 7. The probe wire 705 is connected to the first electrical lead 240 via a first probe lead 710. When the first section 105 is engaged with the second section 110, the first probe lead 710 electrically connects the probe wire 705 to the power supply 402 in the second section 110.

As mentioned previously and described in more detail below, the saturation sensor 427 may measure at least one electrical characteristic or determine an impedance across at least a portion of the first section 105. More specifically, for example, the saturation sensor 427 may measure at least one electrical characteristic or determine an impedance across the saturation circuit assembly 700, connecting the probe wire 705 and the heating element 236 to the first electrical lead 240 and the second electrical lead 240'. In various example embodiments, the at least one electrical characteristic may include, but should not be limited to, a resistance, a capacitance, or both.

The control circuitry 428 in the second section 140' may determine an impedance associated with the heating element 236 and the probe wire 705 based on the measured electrical characteristic(s), for example, resistance, measured by the saturation sensor 427. In various example embodiments, the control circuitry 428 may determine a saturation level of the wick 238 based on the impedance or the at least one electrical characteristic.

As the electrical characteristic(s) and resulting impedance are indicative (e.g., directly indicative) of the saturation level of the wick 238, the electrical characteristics and/or impedance may be used to detect depletion of the non-nicotine pre-vapor formulation in the non-nicotine reservoir 232 so that undesired non-nicotine vapor elements will not be generated. In other words, for example, the saturation sensor 427 and measured electrical characteristics may enable detecting of dry wick conditions (also referred to as dry puff conditions), and in turn, depletion of the non-nicotine pre-vapor formulation in the non-nicotine reservoir.

The probe wire 705 may be made of stainless steel; however, any other conductive metal acceptable to product safety may be used. The saturation sensor 427 may implement any suitable method for determining impedance between the heating element 236 and the probe wire 705, such as based on a measured resistance, a measured capacitance, or a measured combination of resistance and capacitance.

As described below, the saturation circuit assembly 700 is sensitive to both the presence and the amount of non-nicotine pre-vapor formulation in the wick 238. For example, when the wick 238 is initially dry, the impedance may have a resistive measurement in excess of about 10 MΩ and a capacitance of about 2 pf. However, once (e.g., within a few seconds) a drop of non-nicotine pre-vapor formulation (e.g., about 5 mg) is placed on one end of the wick 238, the resistive measurement may be about 2 MΩ and the capacitance may be about 200 pf. As further non-nicotine pre-vapor formulation is added, the impedance continues to change, until the wick 238 is saturated. When fully saturated, the wick 238 may have a resistance of about 45 KΩ and a capacitance of about 2200 pf.

According to one or more example embodiments, in response to a resistance greater than or equal to about 101MΩ and/or a capacitance of less than or equal to about 2 pf, the control circuitry 428 may power off or disable vaping at the non-nicotine e-vaping device 10 by cutting off supply of power to the heating element 236. Additionally or alternatively, the control circuitry 428 may generate and display a dry wick alert, by illuminating an indicator light on the non-nicotine e-vaping device 10. The indicator light may be the heat activation light 436 and may illuminate a particular color or flash when the dry wick alert is generated. In various example embodiments, a separate indicator light may be included on the first housing 120 of the non-nicotine e-vaping device 10.

One or more example embodiments may provide more accurate resistance and/or capacitance measurements because the saturation circuit assembly 700 is more directly influenced by the amount of non-nicotine pre-vapor formulation saturating the wick 238 since the wick 238 is in contact with the probe wire 705 and the heating element 236.

Figure 8:
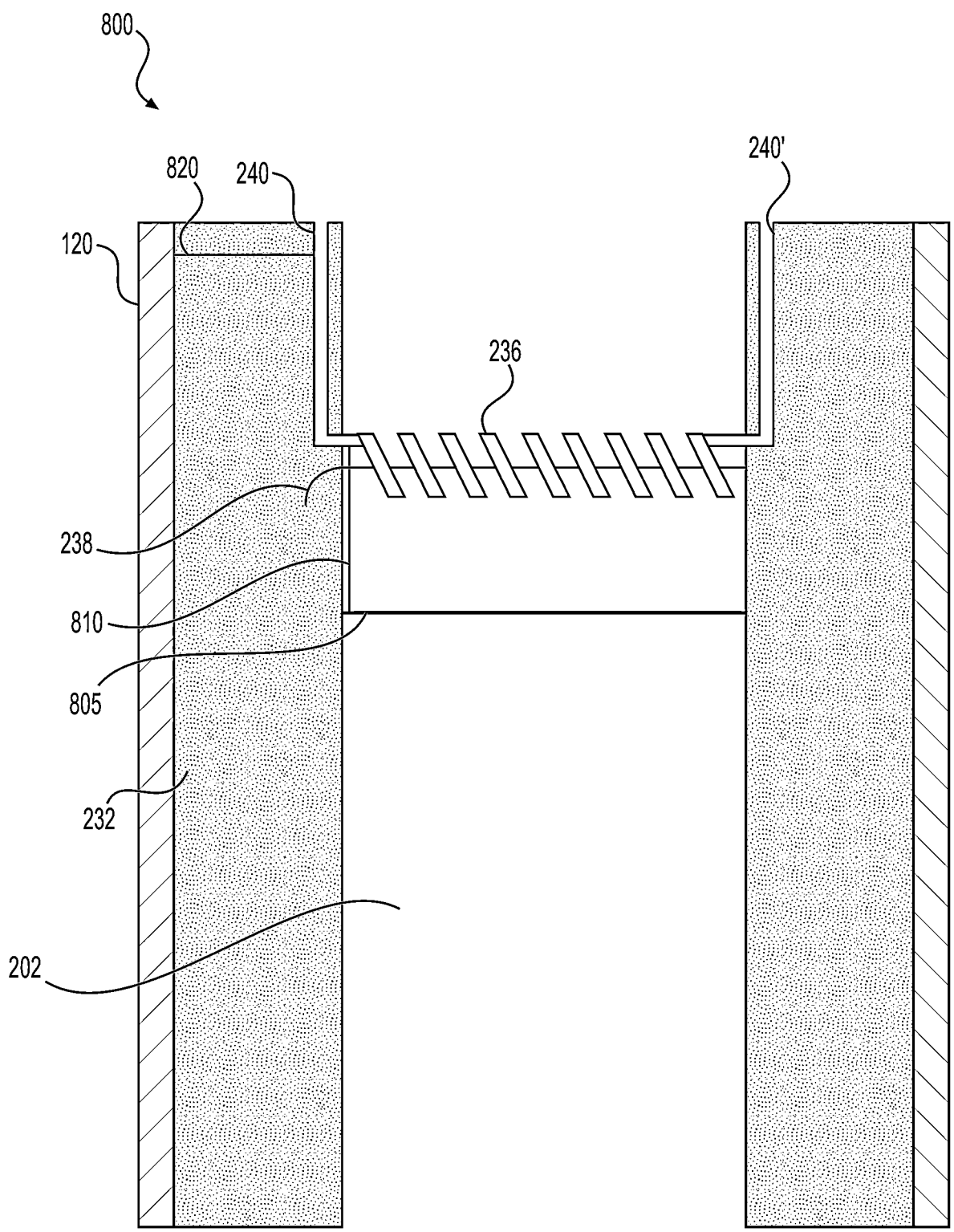
FIG. 8 is a cross-sectional view of another example embodiment of a saturation circuit assembly.
Figure 9:
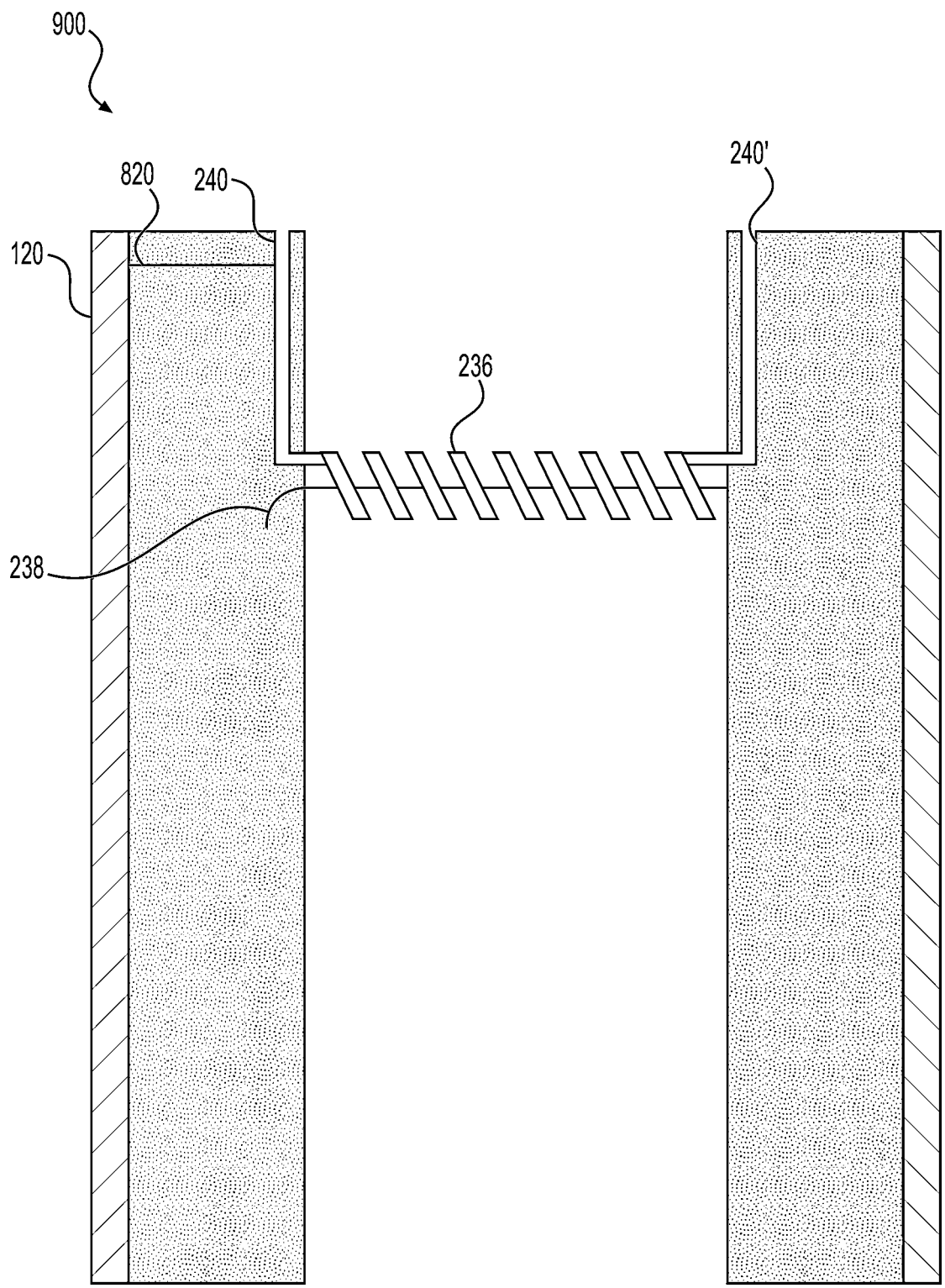
FIG. 9 is a cross-sectional view of another example embodiment of a saturation circuit assembly.

Additionally, non-nicotine pre-vapor formulations include glycerin, propylene glycol, and water, while other constituents are present in smaller quantities. Therefore, the non-nicotine pre-vapor formulation acts as an electrolyte in the capacitor formed between the heating element 236 and the probe wire 705 (or the first housing 120, as shown in FIGS. 8 and 9). Therefore, the amount of non-nicotine pre-vapor formulation present more directly influences the capacitance of the saturation sensor 427.

Since the non-nicotine pre-vapor formulation is not an insulator, the non-nicotine pre-vapor formulation allows the passage of electrical current, which can be measured readily to determine a resistance. Both the capacitance and the resistance vary directly with the amount of non-nicotine pre-vapor formulation on (also referred to as saturation level of) the wick 238. Either or both may be measured to determine that the amount of non-nicotine pre-vapor formulation on the wick 238 is decreasing (or has decreased) below a minimum threshold level (e.g., the wick 238 is beginning to dry). The combination of resistance and capacitance may be used to determine the electrical impedance of the wick 238.

When non-nicotine pre-vapor formulation is heated to generate non-nicotine vapor, the saturation level of the wick 238 decreases, and additional non-nicotine pre-vapor formulation flows into the wick 238 from the non-nicotine reservoir (e.g., via capillary action) to replenish the wick 238. As a result, a flow rate at which the saturation level of the wick 238 is replenished may be determined.

The control circuitry 428 may compare the flow or refill rate with a minimum flow rate threshold to determine whether the non-nicotine pre-vapor formulation in the non-nicotine reservoir is becoming depleted. If the flow rate is below the minimum flow rate threshold, the control circuitry 428 determines that the non-nicotine pre-vapor formulation in the non-nicotine reservoir is becoming depleted, and may output a corresponding indication or alert to the adult vaper. The indication or alert may be illuminating an indicator light (simply powering on the light or performing a flashing pattern).

Calculation of a flow or refill rate for the wick 238 will be discussed in more detail below with regard to FIG. 11.

Moreover, the electrical characteristics measurements may be performed while the non-nicotine e-vaping device 10 is operational (e.g., during a puff when power is applied to the heating element 236) and may be performed using the first electrical lead 240 and the second electrical lead 240', without the need for an additional third electrical lead from the first section 105 to the second section 110.

While being described within the non-nicotine e-vaping device 10, the saturation sensor 427 and the saturation circuit assembly 700 may be implemented on a wick included in paint or ink systems, food systems implementing a wicking of flavoring or other ingredients, a feedback system to increase a wicking refill rate, medical systems to detect saturation of a bandage, etc. Because the saturation sensor 427 and the saturation circuit assembly 700 are sensitive, the described system could be used to detect an increase of a liquid presence or level before the liquid begins to accumulate in a protected area, increasing the various applications of the system.

FIG. 8 is a cross-sectional view of another example embodiment of a saturation circuit assembly 800. FIG. 8 depicts a portion of the first section 105 of the non-nicotine e-vaping device 10, enhancing the view of the heating element 236. The saturation circuit assembly 800 of FIG. 8 is similar to the example embodiment shown in FIG. 7 except that the saturation circuit assembly 800 includes a probe wire 805 around the air tube 202 that is connected to the first electrical lead 240. In various example embodiments, the probe wire 805 may be connected to the second electrical lead 240'.

A first probe lead 810 connects one end of the probe wire 805 to the first electrical lead 240. Additionally, the first housing 120 is connected to the first electrical lead 240 via a first housing lead 820. The saturation sensor 427 measures a resistance and/or a capacitance between the probe wire 805 and the first housing 120 to determine the amount of non-nicotine pre-vapor formulation in the non-nicotine reservoir 232. Then, as described above, the control circuitry 428 disables the non-nicotine e-vaping device 10 and/or outputs an alert of an empty, low, or near depleted non-nicotine reservoir 232 accordingly. In various example embodiments, the saturation circuit assembly 800 may exclude the first housing lead 820 and instead measure the resistance and/or capacitance across the probe wire 805 and the heating element 236. As mentioned similarly above, the probe wire 805 is configured to circumscribe the air tube 202.

FIG. 9 is a cross-sectional view of another example embodiment of a saturation circuit assembly 900. FIG. 9 depicts a portion of the first section 105 of the non-nicotine e-vaping device 10, enhancing the view of the heating element 236. The saturation circuit assembly 900 of FIG. 9 is similar to the example embodiment shown in FIG. 8 except that the saturation circuit assembly 900 excludes the probe wire 805. Instead, the saturation sensor 427 measures a resistance and/or a capacitance across the heating element 236 and the first housing 120 to determine a saturation level of the wick 238.

Figure 10:
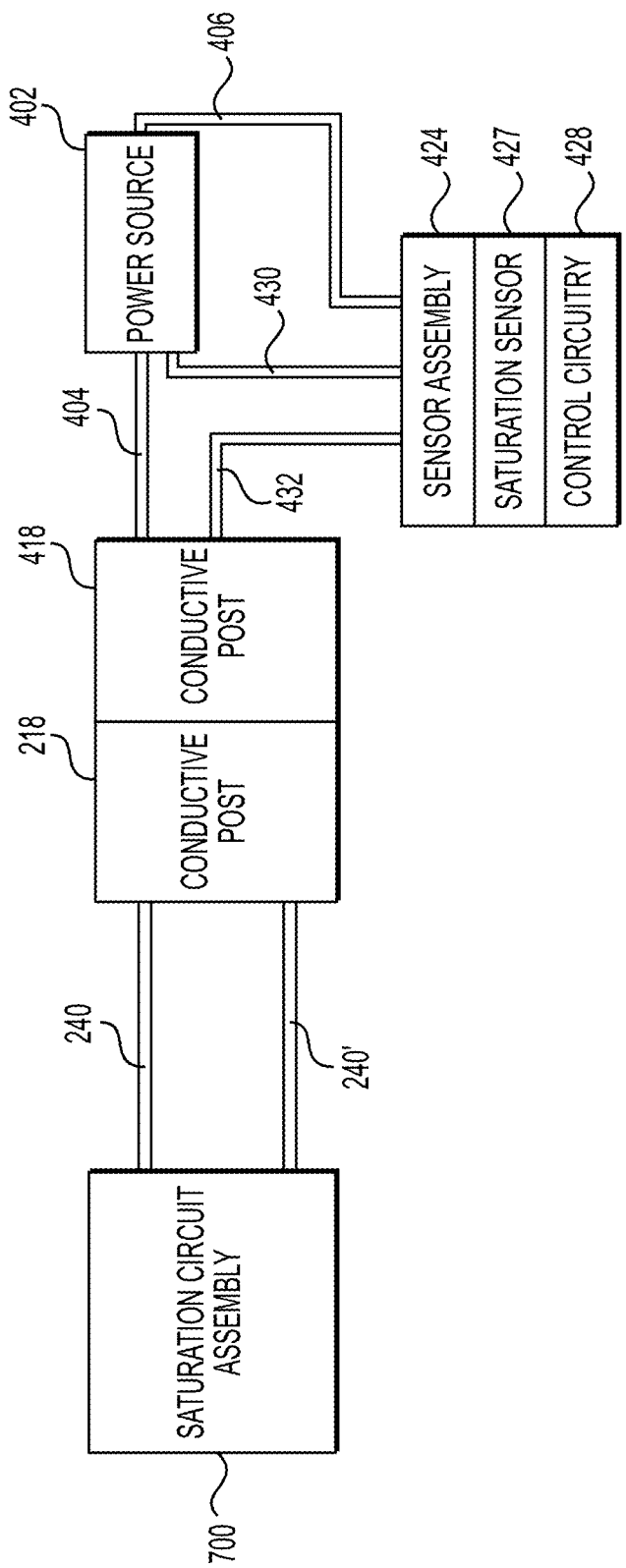
FIG. 10 is a block diagram of saturation determination circuit arrangement.

FIG. 10 is a block diagram of an example embodiment of a saturation determination circuit arrangement. The saturation circuit assembly 700 of FIG. 7 is electrically coupled to the power supply 402, the sensor assembly 424, the saturation sensor 427, and the control circuitry 428 via various electrical leads (the first electrical lead 240, the second electrical lead 240', the anode connection 404, the cathode connection 406, control circuitry wiring 430 and 432), and conductive posts 218 and 418. The saturation sensor 427 measures a resistance and/or a capacitance across the saturation circuit assembly 700. The same saturation determination circuit arrangement may be used with the saturation circuit assembly 800 of FIG. 8 and the saturation circuit assembly 900 of FIG. 9.

The control circuitry 428 may include a non-volatile memory (not shown) storing impedance thresholds, resistance thresholds, capacitance thresholds, flow or refill rate thresholds, etc.

Figure 11:
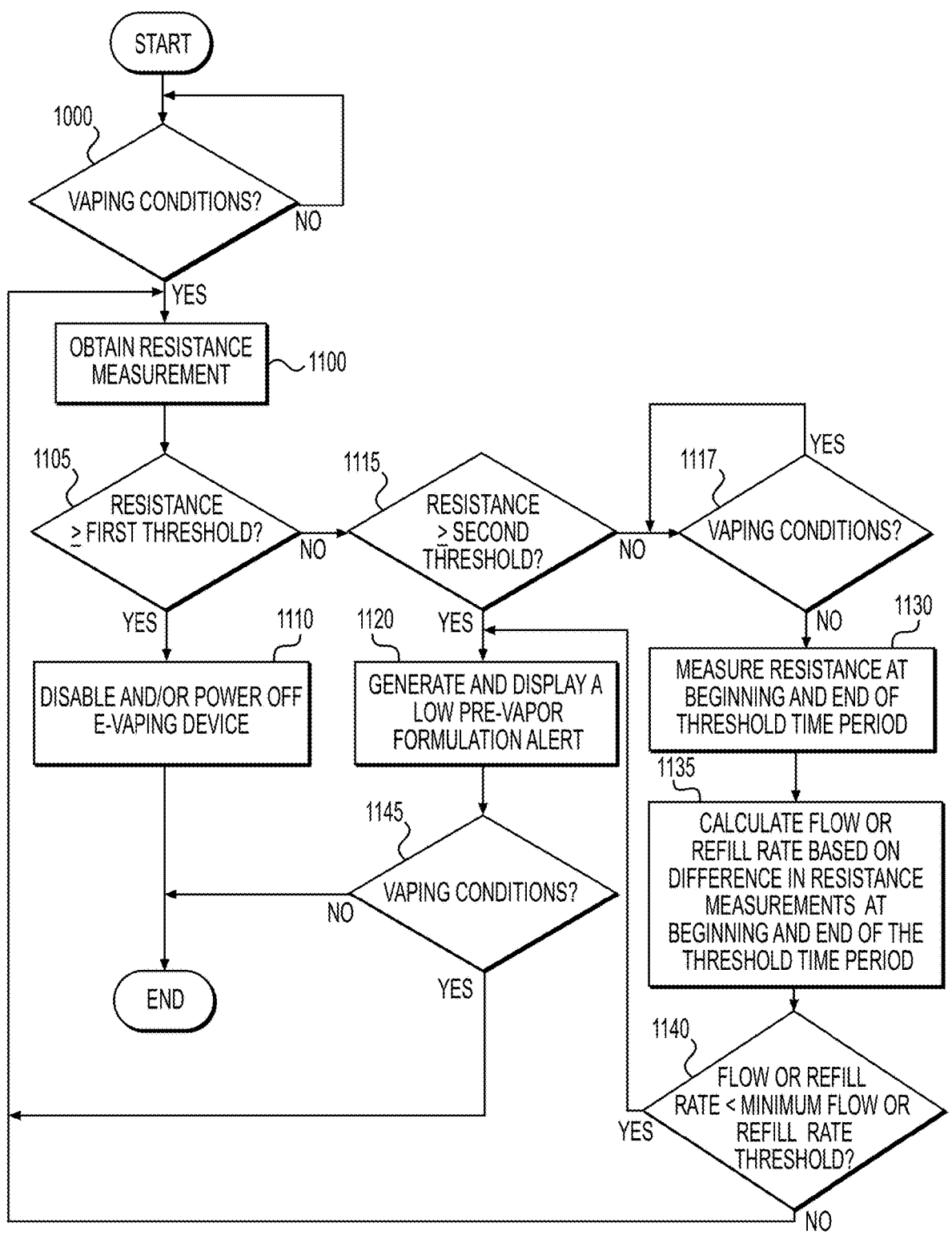
FIG. 11 is a flow diagram of a method for non-nicotine pre-vapor formulation depletion detection according to example embodiments.

FIG. 11 is a flow diagram illustrating a method for non-nicotine pre-vapor formulation depletion detection.

For example purposes, the example embodiment shown in FIG. 11 will be discussed with regard to resistance and with regard to the example embodiment shown in FIG. 7. However, example embodiments should not be limited to this example. Rather, the control circuitry 428 may perform the method shown in FIG. 11 based on measured capacitance or impedance of the wick 238. In one example, the control circuitry 428 may measure capacitance of the wick 238, which may then be utilized in place of resistance in the method shown in FIG. 11. In another example, the control circuitry 428 may measure resistance and capacitance of the wick 238, which may then be utilized to compute and/or determine an impedance of the wick 238. The impedance of the wick 238 may then be utilized in place of the resistance in the method shown in FIG. 11. Moreover, the control circuitry 428 may perform a similar method based on information obtained from the example embodiments of the saturation circuit assembly shown in FIGS. 8 and 9.

Referring to FIG. 11, at 1000 the control circuitry 428 determines whether vaping conditions exist at the non-nicotine e-vaping device 10. According to at least one example embodiment, the control circuitry 428 may determine whether vaping conditions exist at the non-nicotine e-vaping device 10 based on output from the sensor assembly 424. In one example, if the output from the sensor assembly 424 indicates application of negative pressure above a threshold at the mouthpiece 125 of the non-nicotine e-vaping device 10, then the control circuitry 428 determines that vaping conditions exist at the non-nicotine e-vaping device 10.

If the control circuitry 428 determines that vaping conditions exist, then at 1100 the control circuitry 428 measures (or causes the saturation circuit assembly 700 to measure) the resistance of the wick 238. As mentioned above, although the example embodiment shown in FIG. 11 is discussed with regard to resistance, the control circuitry 428 may measure and/or determine at least one electrical characteristic of the wick 238, wherein the at least one electrical characteristic may include a resistance and/or a capacitance of the wick 238, or an impedance of the wick 238, which is determined based on the resistance and/or capacitance.

At 1105, the control circuitry 428 determines whether the measured resistance of the wick 238 is greater than or equal to a first threshold (e.g., about 10 MΩ).

If the measured resistance of the wick 238 is greater than or equal to the first threshold, then at 1110 the control circuitry 428 disables the non-nicotine e-vaping device 10. In at least one example embodiment, disabling of the non-nicotine e-vaping device 10 may include disabling vaping function by cutting off power to the heating element 236 or causing the non-nicotine e-vaping device 10 to power off (or enter a low power state). The process then terminates. Although not shown, at 1110 the control circuitry 428 may also cause the heat activation light 436 to illuminate in a particular color indicating that the wick 238 is dry and/or the non-nicotine reservoir 232 is depleted.

Returning to 1105, if the control circuitry 428 determines that the measured resistance is less than the first threshold, then at 1115 the control circuitry 428 determines whether the measured resistance is above a second threshold (e.g., about 2 MΩ).

If the measured resistance is above the second threshold (and thus, between about 10 MΩ and about 2 MΩ), then at 1120 the control circuitry 428 generates and displays a non-nicotine pre-vapor formulation low alert, such as by illuminating the heat activation light 436.

At 1145, the control circuitry 428 determines whether vaping conditions still exist in the same or substantially the same manner as discussed above with regard to 1000.

If vaping conditions still exist, then the process returns to 1100 and continues as discussed herein.

Returning to 1145, if vaping conditions no longer exist (e.g., the puff has ended), then the process terminates.

Returning to 1115, if the measured resistance is less than the second threshold, then at 1117 the control circuitry 428 determines whether vaping conditions still exist (whether the current puff has ended) in the same or substantially the same manner as discussed above with regard to 1000.

If vaping conditions no longer exist, then at 1130 the control circuitry 428 measures the resistance of the wick 238 at the time when the vaping conditions ceased and again at the end of a threshold time period (e.g., 0.5, 1, or 2 seconds).

At 1135, the control circuitry 428 calculates a refill rate or a flow rate based on the difference between the saturation level (indicated by resistance measurement) at the end of the puff and the saturation level (indicated by resistance measurement) at the end of the threshold time period. In this case, the saturation level may be indicated by the measured resistance level $R_0$ of the wick 238 at the end of the puff (first time) and the measured resistance level $R_1$ of the wick 238 at the end of the threshold time period after the puff has ended (second time). In one example, the control circuitry 428 may compute the refill rate as the change in resistance level divided by the length of the threshold time period $$t_{TH}\left(\text{REFILL\_RATE} = \frac{R_0 - R_1}{t_{TH}}\right).$$

in another example in which impedance is used, the refill rate may be computed as the change in impedance level divided by the length of the threshold time period; that is, $$\left(\text{REFILL\_RATE} = \frac{Z_0 - Z_1}{t_{TH}}\right),$$

where $Z_0$ is the impedance of the wick 238 at the end of the puff, and $Z_1$ is the impedance of the wick at the end of the threshold time period after the end of the puff.

In at least one other example embodiment, the control circuitry 428 may calculate the flow or refill rate by monitoring the resistance, capacitance and/or impedance of the wick 238 during a puff to determine a minimum saturation level (e.g., maximum resistance or impedance value) and then when the wick 238 becomes re-saturated (reaches its initial resistance or impedance level). The control circuitry 428 may then compute the flow rate as the amount of re-saturation (difference between the impedance at depletion and re-saturation, which may be indicated by resistance measurements) over the time between when the wick 238 is at the minimum saturation level and when the wick 238 is re-saturated.

At 1140, the control circuitry 428 compares the refill rate computed at 1135 with a minimum refill rate threshold to determine whether the refill rate is less than the minimum refill rate threshold.

As the amount of non-nicotine pre-vapor formulation in the non-nicotine reservoir 232 decreases, the refill rate for the wick 238 decreases. Thus, the control circuitry 428 may determine that the non-nicotine pre-vapor formulation in the non-nicotine reservoir 232 is becoming depleted (falls below a minimum threshold) when the refill rate for the wick falls below a minimum threshold level.

If the control circuitry 428 determines that the refill rate is below the minimum threshold at 1140, then the control circuitry 428 determines that the non-nicotine pre-vapor formulation in the non-nicotine reservoir 232 is becoming depleted (is low). Accordingly, the process proceeds to 1120 and continues as discussed herein.

Returning to 1140, if the refill rate is greater than the minimum refill rate threshold, then the process returns to 1100 and continues as discussed herein.

Returning to 1117, if the control circuitry 428 determines that vaping conditions still exist, then the control circuitry 428 continues to monitor output of the sensor assembly 424 to determine when the vaping conditions cease (the puff has ended). Once vaping conditions are no longer present, the process proceeds to 1130 and continues as discussed above.

Returning now to 1000 in FIG. 11, if the control circuitry 428 determines that vaping conditions are not yet present, then the control circuitry 428 continues to monitor output of the sensor assembly 424 for vaping conditions. Once vaping conditions are detected, the process proceeds to 1100 and continues as discussed above.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present Like numbers refer to like elements throughout the specification. As used herein, the term "and/or" includes any and all combinations of one or more of the associated listed items.

It should be understood that, although the terms first, second, third, or the like, may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

In an example embodiment, a flavoring (at least one flavorant) and/or a non-nicotine compound is included in the non-nicotine pre-vapor formulation. In an example embodiment, the non-nicotine pre-vapor formulation is a liquid, solid, dispersion and/or a gel formulation including, but not limited to, water, beads, solvents, active ingredients, ethanol, plant extracts, natural or artificial flavors, and/or at least one non-nicotine vapor former such as glycerin and propylene glycol.

The non-nicotine compound is devoid of nicotine. In an example embodiment, the non-nicotine compound does not include tobacco, nor is the compound derived from tobacco. In an example embodiment, the non-nicotine compound is *cannabis*, or includes at least one *cannabis*-derived constituent. In an example embodiment, a *cannabis*-derived constituent includes at least one of a *cannabis*-derived cannabinoid (e.g., a phytocannabinoid, or a cannabinoid synthesized by a *cannabis* plant), at least one *cannabis*-derive terpene, at least one *cannabis*-derived flavonoid, or combinations thereof.

In an example embodiment, the non-nicotine compound is in the form of, or included in, a solid, a semi-solid, a gel, a hydrogel, or combinations thereof, and the non-nicotine compound is infused into, or co-mingled or combined within, the non-nicotine pre-vapor formulation. In an example embodiment, the non-nicotine compound is in the form of, or included in, a liquid or a partial-liquid, that includes an extract, an oil, a tincture, a suspension, a dispersion, a colloid, an alcohol, a general non-neutral (slightly acidic or slightly basic) solution, or combinations thereof, and the non-nicotine compound is infused into, or comingled or combined within, the non-nicotine pre-vapor formulation. In an example embodiment, the non-nicotine compound is a constituent of the non-nicotine pre-vapor formulation. In an example embodiment, the non-nicotine pre-vapor formulation is, or is part of, a dispersion, a suspension, a gel, a hydrogel, a colloid, or combinations thereof, and the non-nicotine compound is a constituent of the non-nicotine pre-vapor formulation.

In an example embodiment, the non-nicotine compound undergoes a slow, natural decarboxylation process over an extended duration of time at low temperatures, including at or below room temperature (72° F.). In an example embodiment, the non-nicotine compound may undergo a significantly elevated decarboxylation process, on the order of 50% decarboxylation or greater if the non-nicotine compound is exposed to elevated temperatures especially in the range of about 175° F. or greater over a period of time (minutes or hours, at a relatively low pressure such as 1 atmosphere), where even further elevated temperatures (about 240° F. or greater) can cause a rapid or instantaneous decarboxylation to occur at a potentially high decarboxylation rate (50% or more), though ever further elevated temperatures can cause a degradation of some or all of the chemical properties of the non-nicotine compounds.

In an example embodiment, the at least one non-nicotine vapor former of the non-nicotine pre-vapor formulation includes diols (such as propylene glycol and/or 1, 3-propanediol), glycerin and combinations, or sub-combinations, thereof. Various amounts of non-nicotine vapor former may be used. For example, in some example embodiments, the at least one non-nicotine vapor former is included in an amount ranging from about 20% by weight based on the weight of the non-nicotine pre-vapor formulation to about 90% by weight based on the weight of the non-nicotine pre-vapor formulation (for example, the non-nicotine vapor former is in the range of about 50% to about 80%, or about 55% to 75%, or about 60% to 70%), etc. As another example, in an example embodiment, the non-nicotine pre-vapor formulation includes a weight ratio of the diol to glycerin that ranges from about 1:4 to 4:1, where the diol is propylene glycol, or 1,3-propanediol, or combinations thereof. In an example embodiment, this ratio is about 3:2. Other amounts or ranges may be used.

In an example embodiment, the non-nicotine pre-vapor formulation includes water. Various amounts of water may be used. For example, in some example embodiments, water may be included in an amount ranging from about 5% by weight based on the weight of the non-nicotine pre-vapor formulation to about 40% by weight based on the weight of the non-nicotine pre-vapor formulation, or in an amount ranging from about 10% by weight based on the weight of the non-nicotine pre-vapor formulation to about 15% by weight based on the weight of the non-nicotine pre-vapor formulation. Other amounts or percentages may be used. For example, in an example embodiment, the remaining portion of the non-nicotine pre-vapor formulation that is not water (and not the non-nicotine compound and/or flavorants), is the non-nicotine vapor former (described above), where the non-nicotine vapor former is between 30% by weight and 70% by weight propylene glycol, and the balance of the non-nicotine vapor former is glycerin. Other amounts or percentages may be used.

In an example embodiment, the non-nicotine pre-vapor formulation includes at least one flavorant in an amount ranging from about 0.2% to about 15% by weight (for instance, the flavorant may be in the range of about 1% to 12%, or about 2% to 10%, or about 5% to 8%). In an example embodiment, the at least one flavorant includes volatile *cannabis* flavor compounds (flavonoids). In an example embodiment, the at least one flavorant includes flavor compounds instead of, or in addition to, the *cannabis* flavor compounds. In an example embodiment, the at least one flavorant may be at least one of a natural flavorant, an artificial flavorant, or a combination of a natural flavorant and an artificial flavorant. For instance, the at least one flavorant may include menthol, wintergreen, peppermint, cinnamon, clove, combinations thereof, and/or extracts thereof. In addition, flavorants may be included to provide herb flavors, fruit flavors, nut flavors, liquor flavors, roasted flavors, minty flavors, savory flavors, combinations thereof, and any other desired flavors.

In an example embodiment, the non-nicotine compound may be a medicinal plant, or a naturally occurring constituent of the plant that has a medically-accepted therapeutic effect. The medicinal plant may be a *cannabis* plant, and the constituent may be at least one *cannabis*-derived constituent. Cannabinoids (phytocannabinoids) are an example of a *cannabis*-derived constituent, and cannabinoids interact with receptors in the body to produce a wide range of effects. As a result, cannabinoids have been used for a variety of medicinal purposes. *Cannabis*-derived materials may include the leaf and/or flower material from one or more species of *cannabis* plants, or extracts from the one or more species of *cannabis* plants. In an example embodiment, the one or more species of *cannabis* plants includes *Cannabis sativa, Cannabis indica*, and *Cannabis ruderalis*. In some example embodiments, the non-nicotine pre-vapor formulation includes a mixture of *cannabis* and/or *cannabis*-derived constituents that are, or are derived from, 60-80% (e.g., 70%) *Cannabis sativa* and 20-40% (e.g., 30%) *Cannabis indica*.

Examples of *cannabis*-derived cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (TUCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from the heater 60 may cause decarboxylation to convert tetrahydrocannabinolic acid (THCA) in the non-nicotine pre-vapor formulation to tetrahydrocannabinol (THC), and/or to convert cannabidiolic acid (CBDA) in the non-nicotine pre-vapor formulation to cannabidiol (CBD).

In instances where both tetrahydrocannabinolic acid (THCA) and tetrahydrocannabinol (THC) are present in the non-nicotine pre-vapor formulation, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC), via the decarboxylation process, during the heating of the non-nicotine pre-vapor formulation for purposes of vaporization. Similarly, in instances where both cannabidiolic acid (CBDA) and cannabidiol (CBD) are present in the non-nicotine pre-vapor formulation, the decarboxylation and resulting conversion will cause a decrease in cannabidiolic acid (CBDA) and an increase in cannabidiol (C D). At least 50% (e.g., at least 87%) of the cannabidiohc acid (CID A) may be converted to cannabidiol (CBD), via the decarboxylation process, during the heating of the non-nicotine pre-vapor formulation for purposes of vaporization.

The non-nicotine pre-vapor formulation may contain the non-nicotine compound that provides the medically-accepted therapeutic effect (e.g., treatment of pain, nausea, epilepsy, psychiatric disorders). Details on methods of treatment may be found in U.S. application Ser. No. 15/845,501, filed Dec. 18, 2017, titled "VAPORIZING DEVICES AND METHODS FOR DELIVERING A COMPOUND USING THE SAME," the disclosure of which is incorporated herein in its entirety by reference.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A non-nicotine e-vaping device comprising:
   a saturation sensor configured to
      measure at least one electrical characteristic of a wick at a first time, and
      measure the at least one electrical characteristic of the wick at a second time, the second time being subsequent to the first time; and
   control circuitry configured to cause the non-nicotine e-vaping device to
      calculate a refill rate at which a non-nicotine pre-vapor formulation flows onto the wick based on the at least one electrical characteristic at the first time and the at least one electrical characteristic at the second time,
      determine that the refill rate is less than a threshold refill rate, and
      output a low non-nicotine pre-vapor formulation alert in response to determining that the refill rate is less than the threshold refill rate.

2. The non-nicotine e-vaping device of claim 1, wherein the control circuitry is configured to cause the non-nicotine e-vaping device to calculate the refill rate based on a difference between the at least one electrical characteristic at the first time and the at least one electrical characteristic at the second time.

3. The non-nicotine e-vaping device of claim 1, wherein the control circuitry is configured to cause the non-nicotine e-vaping device to
   compute a first impedance based on the at least one electrical characteristic at the first time,
   compute a second impedance based on the at least one electrical characteristic at the second time, and
   calculate the refill rate based on a difference between the first impedance and the second impedance.

4. The non-nicotine e-vaping device of claim 1, further comprising:
   a non-nicotine reservoir configured to hold a non-nicotine pre-vapor formulation;
   the wick, wherein the wick is configured to draw the non-nicotine pre-vapor formulation from the non-nicotine reservoir;
   a heating element configured to heat the non-nicotine pre-vapor formulation drawn from the non-nicotine reservoir; and
   a probe wire along a length of the wick, the probe wire being separated from the heating element by the wick.

5. The non-nicotine e-vaping device of claim 4, wherein the at least one electrical characteristic of the wick is measured between the heating element and the probe wire.

6. The non-nicotine e-vaping device of claim 4, wherein the probe wire is a stainless steel wire.

7. The non-nicotine e-vaping device of claim 1, wherein the control circuitry is configured to cause the non-nicotine e-vaping device to
   measure the at least one electrical characteristic of the wick at a third time,
   determine that the at least one electrical characteristic at the third time is greater than or equal to a threshold value, and
   disable vaping at the non-nicotine e-vaping device in response to determining that the at least one electrical characteristic at the third time is greater than or equal to the threshold value.

8. The non-nicotine e-vaping device of claim 1, wherein the control circuitry is configured to cause the non-nicotine e-vaping device to
   measure the at least one electrical characteristic of the wick at a third time,
   determine that the at least one electrical characteristic at the third time is greater than or equal to a threshold value, and
   output the low non-nicotine pre-vapor formulation alert in response to determining that the at least one electrical characteristic at the third time is greater than or equal to the threshold value.

9. The non-nicotine e-vaping device of claim 1, wherein the control circuitry is configured to cause the non-nicotine e-vaping device to
   measure the at least one electrical characteristic of the wick at a third time,
   compute an impedance of the wick based on the at least one electrical characteristic at the third time,
   determine that the impedance is greater than or equal to a threshold value, and
   disable vaping at the non-nicotine e-vaping device in response to determining that the impedance is greater than or equal to the threshold value.

10. The non-nicotine e-vaping device of claim 1, wherein the control circuitry is configured to cause the non-nicotine e-vaping device to
    measure the at least one electrical characteristic of the wick at a third time, compute an impedance of the wick based on the at least one electrical characteristic at the third time,
determine that the impedance is greater than or equal to a threshold value, and
output the low non-nicotine pre-vapor formulation alert in response to determining that the impedance is greater than or equal to the threshold value.

11. The non-nicotine e-vaping device of claim 1, further comprising:
a power supply configured to provide power to the non-nicotine e-vaping device.

12. The non-nicotine e-vaping device of claim 1, wherein the at least one electrical characteristic includes a resistance, a capacitance, or both a resistance and a capacitance.

13. A non-nicotine e-vaping device comprising:
an outer housing;
an inner tube coaxially positioned within the outer housing;
a saturation sensor assembly configured to measure at least one electrical characteristic between the outer housing and the inner tube at a first time and a second time, the second time being subsequent to the first time; and
control circuitry configured to cause the non-nicotine e-vaping device to
calculate a refill rate at which a non-nicotine pre-vapor formulation flows onto a wick based on the at least one electrical characteristic at the first time and the at least one electrical characteristic at the second time,
determine that the refill rate is less than a threshold refill rate, and
output a low non-nicotine pre-vapor formulation alert in response to determining that the refill rate is less than the threshold refill rate.

14. The non-nicotine e-vaping device of claim 13, further comprising:
a non-nicotine reservoir configured to hold a non-nicotine pre-vapor formulation, the non-nicotine reservoir positioned between the inner tube and the outer housing;
the wick, wherein the wick is configured to draw the non-nicotine pre-vapor formulation from the non-nicotine reservoir; and
a heating element configured to heat the non-nicotine pre-vapor formulation drawn from the non-nicotine reservoir.

15. The non-nicotine e-vaping device of claim 13, further comprising:
a probe wire around an outer perimeter of the inner tube, wherein
the saturation sensor assembly is configured to measure the at least one electrical characteristic between the outer housing and the inner tube by measuring the at least one electrical characteristic between the outer housing and the probe wire around the outer perimeter of the inner tube.

16. The non-nicotine e-vaping device of claim 15, wherein the probe wire is a stainless steel wire.

17. The non-nicotine e-vaping device of claim 13, wherein the control circuitry is configured to cause the non-nicotine e-vaping device to calculate the refill rate based on a difference between the at least one electrical characteristic at the first time and the at least one electrical characteristic at the second time.

18. The non-nicotine e-vaping device of claim 13, wherein the control circuitry is configured to cause the non-nicotine e-vaping device to
compute a first impedance based on the at least one electrical characteristic at the first time,
compute a second impedance based on the at least one electrical characteristic at the second time, and
calculate the refill rate based on a difference between the first impedance and the second impedance.

19. The non-nicotine e-vaping device of claim 13, wherein the control circuitry is configured to cause the non-nicotine e-vaping device to
measure the at least one electrical characteristic at a third time,
determine that the at least one electrical characteristic at the third time is greater than or equal to a threshold value, and
disable vaping at the non-nicotine e-vaping device in response to determining that the at least one electrical characteristic at the third time is greater than or equal to the threshold value.

20. The non-nicotine e-vaping device of claim 13, wherein the control circuitry is configured to cause the non-nicotine e-vaping device to
measure the at least one electrical characteristic at a third time,
determine that the at least one electrical characteristic at the third time is greater than or equal to a threshold value, and
output the low non-nicotine pre-vapor formulation alert in response to determining that the at least one electrical characteristic at the third time is greater than or equal to the threshold value.

21. The non-nicotine e-vaping device of claim 13, wherein the control circuitry is configured to cause the non-nicotine e-vaping device to
measure the at least one electrical characteristic at a third time,
compute an impedance of the wick based on the at least one electrical characteristic at the third time,
determine that the impedance is greater than or equal to a threshold value, and
disable vaping at the non-nicotine e-vaping device in response to determining that the impedance is greater than or equal to the threshold value.

22. The non-nicotine e-vaping device of claim 13, wherein the control circuitry is configured to cause the non-nicotine e-vaping device to
measure the at least one electrical characteristic at a third time,
compute an impedance of the wick based on the at least one electrical characteristic at the third time,
determine that the impedance is greater than or equal to a threshold value, and
output the low non-nicotine pre-vapor formulation alert in response to determining that the impedance is greater than or equal to the threshold value.

* * * * *